(12) United States Patent
Sato

(10) Patent No.: US 7,041,960 B2
(45) Date of Patent: May 9, 2006

(54) BOND SEPARATION INSPECTION METHOD USING COMPRESSIVE THERMAL STRAIN IN OPTICAL SENSOR PART

(75) Inventor: Keiichi Sato, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 70 days.

(21) Appl. No.: 10/824,353

(22) Filed: Apr. 15, 2004

(65) Prior Publication Data

US 2004/0206893 A1 Oct. 21, 2004

(30) Foreign Application Priority Data

Apr. 18, 2003 (JP) .............................. 2003-114786

(51) Int. Cl.
*G01J 4/00* (2006.01)
*G01N 21/25* (2006.01)

(52) U.S. Cl. ..................... 250/227.18; 250/227.14; 250/227.23; 385/12; 385/80; 73/800; 73/827; 73/150 A

(58) Field of Classification Search ............... 73/150 A
See application file for complete search history.

(56) References Cited

U.S. PATENT DOCUMENTS

| | | | | |
|---|---|---|---|---|
| 5,250,802 A | * | 10/1993 | Runner ............... | 250/227.15 |
| 5,841,034 A | * | 11/1998 | Ball ................... | 73/800 |
| 6,218,661 B1 | * | 4/2001 | Schroeder et al. ..... | 250/227.14 |
| 6,668,105 B1 | * | 12/2003 | Chen et al. .......... | 385/13 |
| 6,756,580 B1 | * | 6/2004 | Schulz et al. ........ | 250/227.14 |
| 6,781,113 B1 | * | 8/2004 | Ogura ................. | 250/227.14 |
| 2002/0117608 A1 | * | 8/2002 | Ogura ................. | 250/227.14 |
| 2005/0129365 A1 | * | 6/2005 | Johnson et al. ........ | 385/37 |

FOREIGN PATENT DOCUMENTS

| JP | 9101255 A | 4/1997 |
|---|---|---|
| JP | 2001021384 A | 1/2001 |

OTHER PUBLICATIONS

Ishikawa, Shinji. *High resolution sensing methods using optical fiber gratings*. Sumitomo Electric Industries, LTD. Yokohama Research Laboratories. Sakai-ku, Yokohama, 244-8588. pp. 648-654. (2000).

* cited by examiner

*Primary Examiner*—Stephone B. Allen
*Assistant Examiner*—Davienne Monbleau
(74) *Attorney, Agent, or Firm*—Birch, Stewart, Kolasch, & Birch, LLP.

(57) ABSTRACT

A bond separation inspection method using an optical fiber sensor. The method includes a step of embedding a sensor part of an optical fiber sensor in an adhesive joining a plurality of members together. The sensor part is embedded in the adhesive in such a way that the sensor part undergoes a compressive strain. Separation of the bond is detected on the basis of an optical characteristic of the sensor part when light from a light source is directed into the optical fiber sensor.

14 Claims, 11 Drawing Sheets

FIG. 19
(PRIOR ART)
(a)
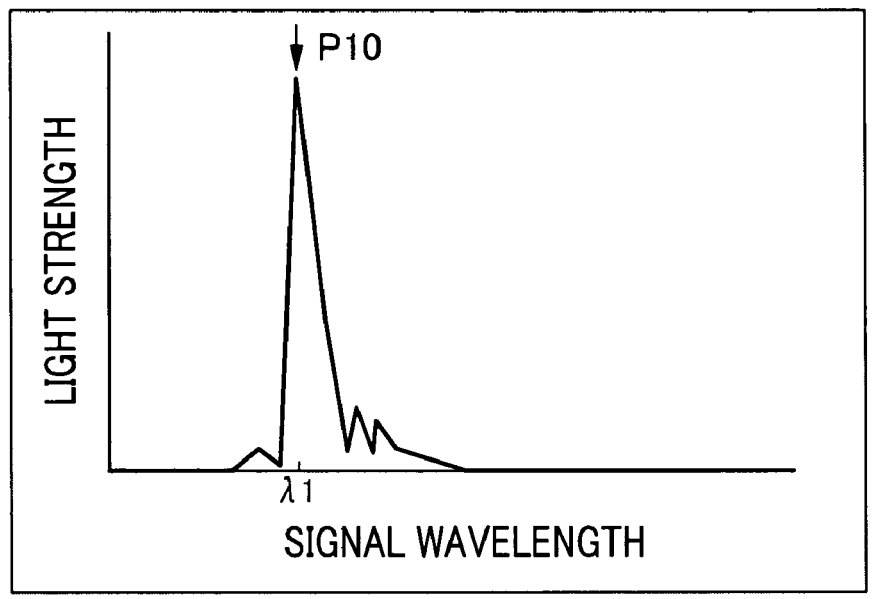
(b)
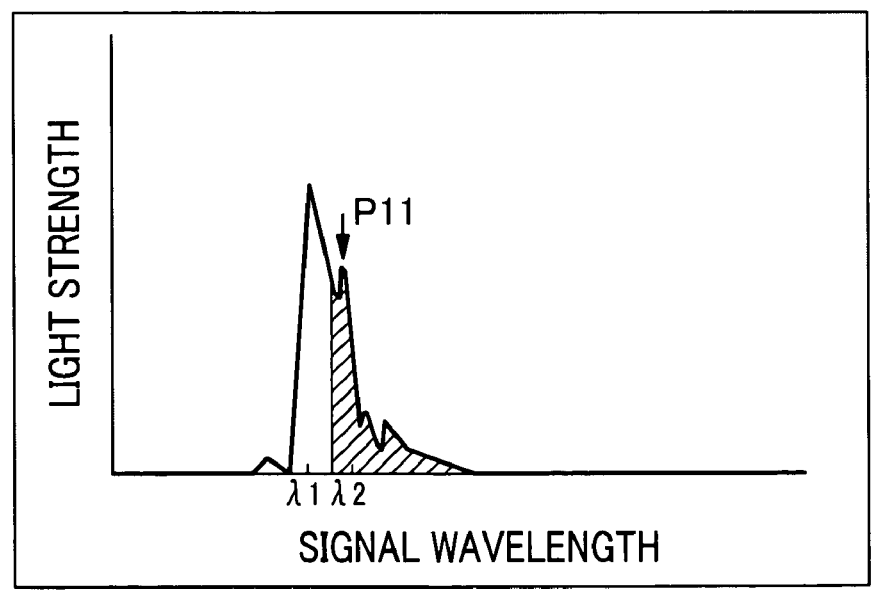

BOND SEPARATION INSPECTION METHOD USING COMPRESSIVE THERMAL STRAIN IN OPTICAL SENSOR PART

This Nonprovisional application claims priority under 35 U.S.C. § 119(a) on Patent Application No(s) . 2003-114786 filed in Japan on Apr. 18, 2003, the entire contents of which are hereby incorporated by reference.

FIELD OF THE INVENTION

This invention relates to a bond separation inspection method, and particularly to a bond separation inspection method using an optical fiber sensor.

BACKGROUND OF THE INVENTION

In related art, in inspecting the soundness of a bond, the presence or otherwise absence of fine cracks in the bond has been checked for visually or by ultrasonic flaw detection. However, even when a skilled inspector checks a joint visually, error-free checking is difficult and also entails a lot of inspection man-hours. Although there have been attempts to evaluate the soundness of bonds using various sensors, difficulty of determination and problems of inspection accuracy have made them unsuitable for practical use.

To solve such problems, technology has been conceived in which a sensor part of an optical fiber sensor is embedded in a bond of joined members or adhered in the vicinity of the bond to assess the state of the joint of the joined members.

An optical fiber sensor is an optical fiber with a sensor part formed in its core part. The sensor part is for example a diffraction grating. An optical fiber sensor having a diffraction grating is called an optical fiber grating sensor. The construction of a sensor part is not limited to a diffraction grating. With an optical fiber sensor, a change in an optical characteristic caused by strain arising in the sensor part is used to measure the joint state. At the time of measurement using an optical fiber sensor, the sensor part of the optical fiber sensor is fixed inside an adhesive when two members are joined together by the adhesive, then light from a broadband light source is introduced into the optical fiber sensor through a light entry end thereof, and changes in reflected light or transmitted light from the sensor part are observed. From this observation, it is possible to ascertain the state of the joint between the joined members.

A measurement method of related art using an optical fiber sensor is disclosed for example in JP-A-9-101255. In this method, converting means, for example an optical fiber sensor, is disposed in the vicinity of a bonded joint. In this method, the converting means is so disposed with respect to the bonded joint that a parameter expressing a characteristic of load displacement between the joined materials and an adhesive can be recorded in correspondence with an applied load. After the assembly of the bonded joint, a reference parameter expressing a characteristic of load displacement between the joined materials and an adhesive with a reference load applied is recorded, and then a parameter expressing a characteristic of load displacement between the joined materials and the adhesive with a test load applied is recorded. The completeness of the joint is then measured by comparing the reference parameter and the parameter obtained thereafter.

Another related art technology using an optical fiber sensor is the separation inspection method of JP-A-2001-21384. In this separation inspection method, first, an optical fiber sensor is fixed to each of two members bonded together. Then, light pulses are inputted through ends of the optical fiber sensors, and strains occurring in the optical fiber sensors are measured from changes in the optical characteristics of scattered light arising in the optical fiber sensors with respect to the inputted light pulses. On the basis of differences in these measured strains of the optical fiber sensors, the occurrence of separation at the contacting faces of the members is detected.

Also, an explanation of precise measurement technology using an optical fiber sensor is set forth in Shinji Ishikawa's 'Applied Physics' Volume 69, Number 6 (2000), page 648 to page 654.

In the case of the method disclosed in the above-mentioned JP-A-9-101255, to check the completeness of a joint it was necessary to apply a load for testing.

In the case of the method disclosed in the above-mentioned JP-A-2001-21384, detection is difficult when the strains caused by separation are not large. The sensor part of an optical fiber sensor can detect surrounding strain as a wavelength change, but when as disclosed in JP-A-9-101255 two members are bonded using an adhesive that hardens at room temperature and the sensor part of the optical fiber sensor is embedded in that adhesive, because even when separation occurs the consequent change in strain is not large, when no load is applied the wavelength change is not large either.

For example, reflected light detection data of when the optical fiber sensor is an optical fiber grating sensor of the kind mentioned above is shown in FIG. 19(a) and (b). FIG. 19(a) is a spectrum of reflected light detected from the optical fiber sensor when separation of the joined members has not occurred. The horizontal axis is wavelength of the reflected light and the vertical axis is light strength of the reflected light. At this time, a reflected light spectrum having a peak P10 at wavelength λ1 is observed. This is because twice the period of the grating becomes an even multiple of the wavelength λ1, and reflected light from the grating at wavelength λ1 mutually enhances so that a reflected light spectrum having a peak at wavelength λ1 is observed.

On the other hand, FIG. 19(b) is a spectrum of reflected light detected from the optical fiber sensor when separation of the joined members has occurred. A small peak P11 appears at a position of wavelength λ2 near wavelength λ1, but there is not an easily distinguishable divide between the two peaks. This is because even when separation occurs, the strain occurring in the grating of the optical fiber sensor is small and the grating period does not change greatly. Because the period of the grating changes under the influence of thermal expansion when the temperature of the optical fiber sensor changes, a change occurs in the position of the peak of the reflected light spectrum when the temperature changes; consequently, the position of the peak changes when the temperature changes even when no separation has occurred, it is difficult to discern whether this is separation, and it becomes impossible to ignore the influence of temperature.

Thus, a bond separation inspection method has been awaited with which it is possible to greatly increase inspection accuracy by making a large change appear in an optical characteristic detected by an optical fiber sensor when joined members have separated.

SUMMARY OF THE INVENTION

A bond separation inspection method provided by the invention includes: a step of joining together two members with an adhesive; a step of embedding a sensor part of an optical fiber sensor in the adhesive; a step of introducing light from a light source into one end of the optical fiber sensor and causing light from the sensor part to emerge from another end of the optical fiber sensor; and a step of detecting separation of the bond of the two members on the basis of an optical characteristic of the light from the sensor part, wherein the step of embedding the sensor part in the adhesive includes a step of applying stress to the sensor part and causing a compressive or tensile strain to arise in the sensor part.

This bond separation inspection method is one in which a sensor part of an optical fiber sensor is embedded in an adhesive joining two members together and separation of the bond is detected on the basis of an optical characteristic of light from the optical fiber sensor when light from a light source is fed into the optical fiber sensor. In particular, when the sensor part of the optical fiber sensor is embedded in the adhesive, because a thermal stress is applied to the sensor part so that it is embedded under a compressive (or tensile) strain, when a small separation starts to occur in the bond, the stress is released, parts where the strain that had arisen in the sensor part of the optical fiber sensor has ceased to exist arise, and consequently the sensor part becomes longer (or shorter) than when it was under strain and a large change arises in its optical characteristic. By observing this optical characteristic, it is possible to detect separation of the bond with good accuracy. Therefore, because it is possible to determine correctly whether or not separation has occurred, there cease to be cases of separation being judged to have occurred and wasteful dismantling of structures being carried out notwithstanding that actually no separation has occurred. That is, it is possible to reduce maintenance costs of structures, and conversely there are no worst cases of structures failing due to separation being judged not to have occurred when in fact it has, so that increased safety of structures can be expected.

In one preferred form of the invention, the sensor part of the optical fiber sensor is embedded in the adhesive with a compressive strain induced therein.

In this bond separation inspection method, preferably, the adhesive is a thermosetting adhesive having an adhesive temperature above room temperature, and the above-mentioned strain is induced in the sensor part by heating the thermosetting adhesive above room temperature to join or bond the two members and then allowing the adhesive to return to room temperature.

By a thermosetting adhesive being used as the adhesive for joining together two members and this being hardened at a temperature higher than room temperature and then returned to room temperature, a compressive strain, for example, can be applied to the sensor part of the optical fiber sensor by means of thermal stress arising due to differential thermal expansion of the adhesive and the optical fiber sensor, and a large compressive strain can be applied to the sensor part. Consequently, when the joined members have separated, parts where the compressive strain has either decreased or ceased to exist arise, and at this time there is a change in the compressive strain in the sensor part and as a result a large change occurs in its optical characteristic. By this means, the separation can be detected with good accuracy.

Another aspect of the invention provides a bond separation inspection method including: a step of joining together two members with an adhesive; a step of embedding a sensor part of an optical fiber sensor in the adhesive; a step of introducing light from a light source into one end of the optical fiber sensor and causing light from the sensor part to emerge from the other end of the optical fiber sensor; and a step of detecting separation of the bond of the two members on the basis of an optical characteristic of the light from the sensor part, and further including a step of applying a predetermined load to the two members.

The above-mentioned predetermined load is preferably a load applied to the two members in a direction such that it tends to increase any separation of the bond.

As described above, separation of the bond is inspected for on the basis of change in an optical characteristic occurring when a predetermined load is applied via the two members, and when the joined members separate under the predetermined load, the strain in the sensor part changes and its optical characteristic also greatly changes. By observing that optical characteristic it is possible to detect separation of the bond with good accuracy. Therefore, because it is possible to determine correctly whether or not separation has occurred, there cease to be cases of separation being judged to have occurred and wasteful dismantling of structures being carried out notwithstanding that actually no separation has occurred; that is, it is possible to reduce maintenance costs of structures, and conversely there are no worst cases of structures failing due to separation being judged not to have occurred when in fact it has, so that increased safety of structures can be expected.

In a separation inspection method according to the invention, preferably, the predetermined load is an external force which elastically deforms a joined member consisting of two members joined together with adhesive. In this case, when the members have separated, because the rigidity of the joined member decreases and when an external force is applied the joined member deforms greatly compared to when separation has not occurred, the strain in the sensor part changes greatly and the optical characteristic also change greatly. By observing that optical characteristic, it is possible to detect separation of the bond with good accuracy.

Preferably, the optical fiber sensor is an optical fiber grating sensor. In this case, as strain of the sensor part a change arises in the grating period, and an optical characteristic of the grating changes. By observing this optical characteristic, separation of the bond can be detected with good accuracy.

Preferably, the light source is a broadband light source. In this case, an optical characteristic can be observed over a broad wavelength range, and it is possible to make observation of the optical characteristic easy and detect separation with good accuracy.

Preferably, the optical characteristic is a reflected light characteristic or a transmitted light characteristic. By observing a reflected light characteristic or a transmitted light characteristic it is possible to detect separation of the bond with good accuracy.

As a reflected light characteristic, for example the spectrum characteristic of reflected light can be used. By observing a change in a reflected light spectrum, it is possible to detect separation of the bond with good accuracy. More specifically, the reflected light characteristic might for example be the reflected light strength characteristic at a predetermined wavelength. Because then a light detector having sensitivity to a predetermined wavelength can be used, it is possible to detect separation of the bond with good accuracy with a simple optical system.

As a transmitted light characteristic, for example the spectrum characteristic of transmitted light can be used. By observing a change in a transmitted light spectrum, it is possible to detect separation of the bond with good accuracy. Also, specifically, the transmitted light characteristic might for example be the transmitted light strength characteristic at a predetermined wavelength. Because then a light detector having sensitivity to a predetermined wavelength can be used, it is possible to detect separation of the bond with good accuracy with a simple optical system.

Preferably, the adhesive is a thermosetting adhesive or a room-temperature thermosetting adhesive.

BRIEF DESCRIPTION OF THE DRAWINGS

A number of presently preferred embodiments of the invention will now be described on the basis of the accompanying drawings, of which:

FIGS. 19(a) and (b) are spectra of reflected light detected from an optical fiber sensor in related art, FIG. 19(a) being a spectrum of light reflected when no separation of joined members has occurred and FIG. 19(b) a spectrum of light reflected when separation of joined members has occurred.

DETAILED DESCRIPTION OF THE PREFERRED EMBODIMENTS

Figure 1:
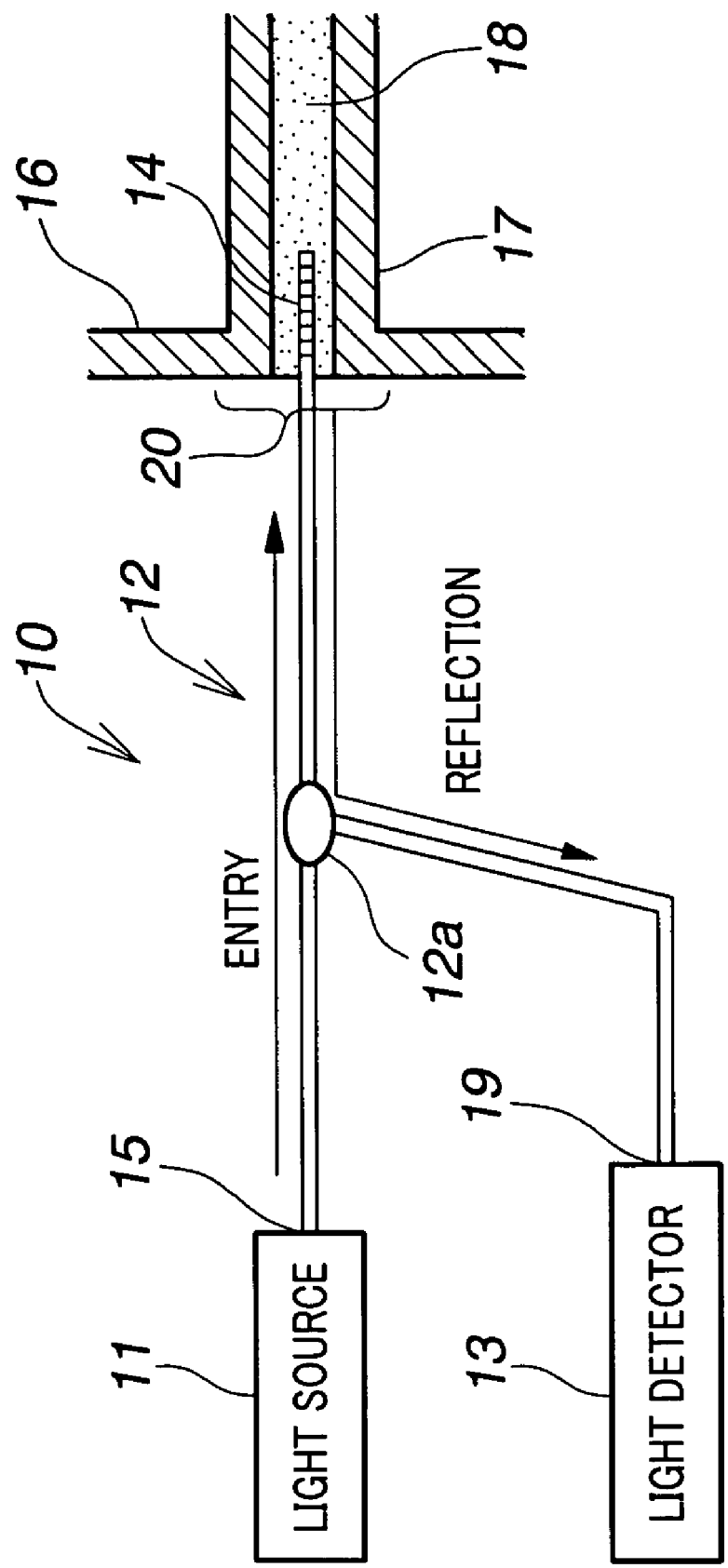
FIG. 1 is a basic construction view of a measuring system used in a separation inspection method according to a first preferred embodiment of the invention for inspecting the inside of an adhesive.

Initial reference is made to FIG. 1 showing the basic construction of a measuring system 10 for carrying out a bond separation inspection method according to a first preferred embodiment of the invention. This measuring system 10 is made up of a light source 11, an optical fiber sensor 12 and a light-detecting part 13.

The light source 11 is a device for directing broadband light through the end face of the entry end of the optical fiber sensor 12, and emits light over a range including light of a wavelength that can be detected by the optical fiber sensor 12. As the light source 11, for example a super-luminescence diode (SLD), a halogen lamp or a tungsten lamp is used, these having continuous broadband spectra.

The optical fiber sensor 12 is made using an optical fiber; a sensor part 14 is formed using the core part of one end of the optical fiber, and a coupler 12a is provided part-way along the optical fiber. The sensor part 14 is formed as a part of the optical fiber. In the optical fiber sensor 12, light from the light source 11 is introduced into one end of the optical fiber, and this light from the light source 11 is guided along the optical fiber to the sensor part 14. Light reflected from the sensor part 14 is guided to the light-detecting part 13 via the coupler 12a and detected by the light-detecting part 13. As the optical fiber sensor, for example an optical fiber grating sensor is used. An optical fiber grating sensor has a diffraction grating as the above-mentioned sensor part and makes use of the optical characteristics of diffraction gratings.

In the following description, an example wherein an optical fiber grating sensor is used as the optical fiber sensor 12 will be described.

The base end 15 of the optical fiber is connected to the light source 11, and the sensor part 14 is provided at the distal end. As will be further discussed later, the sensor part 14 is a diffraction grating part made in the core part of the optical fiber. In the structure of a bond 20 where members 16, 17 are joined together with an adhesive 18 as shown in FIG. 1, the sensor part 14 is embedded within the adhesive 18 used at the time of bonding of members 16 and 17. The distal end 19 of an optical fiber branching from the coupler 12a is connected to the light-detecting part 13.

As the light-detecting part 13, to obtain the spectrum of light reflected from the sensor part 14, for example an optical spectrum analyzer is used.

Figure 2:
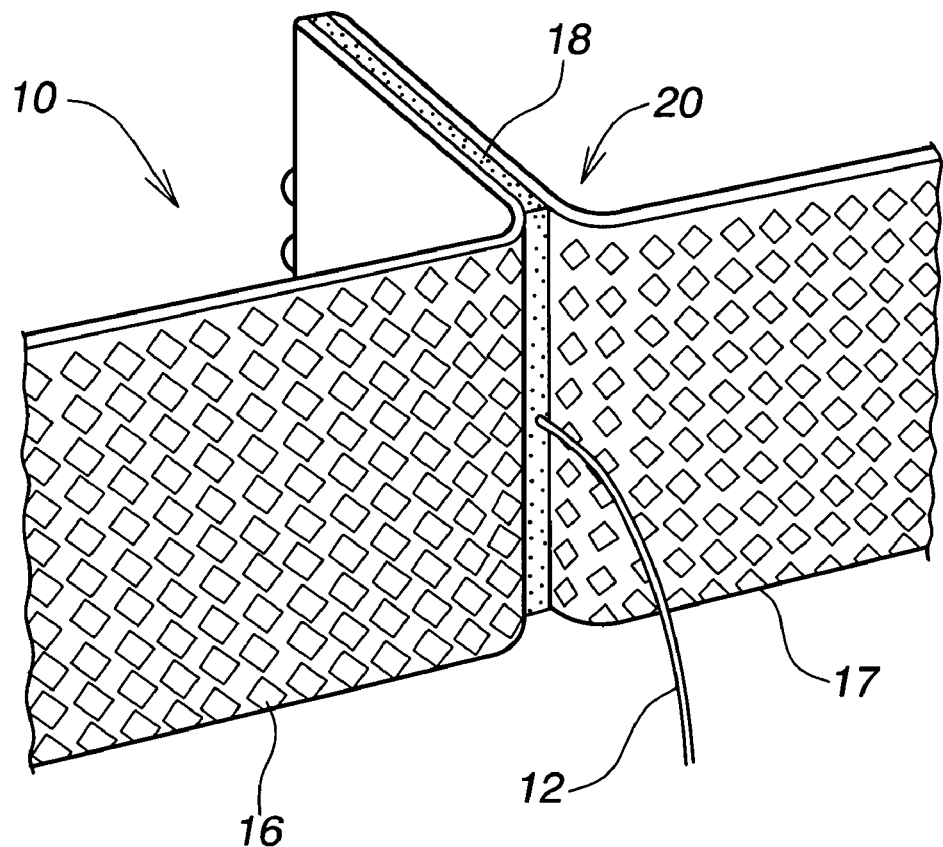
FIG. 2 is a perspective view of a bond with a sensor part embedded in an adhesive.
Figure 3:
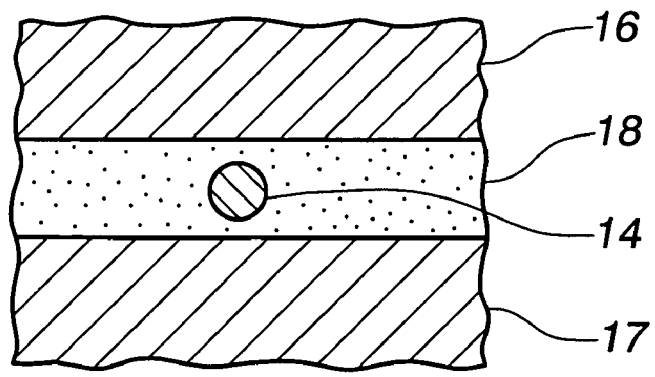
FIG. 3 is an enlarged sectional view of a bond with a sensor part embedded in an adhesive.

Referring to FIG. 2 and FIG. 3, of the bond 20, the location where the sensor part 14 is embedded is a location near a surface of the adhesive 18 of the bond 20 exposed to the outside, where cracking and separation tend to occur. For example, the sensor part 14 is embedded so that the distance from the light-entry-side end of the grating of the sensor part 14 to the surface of the adhesive 18 of the bond 20 exposed to the outside is 0 to 5 mm.

A measuring system 10 like this is used to measure whether separation of the joined member formed by the members 16, 17 and the bond 20 has occurred. In practice, the sensor part 14 is typically embedded in the adhesive 18 of a bond 20 used in the manufacture of an aircraft.

Reference is now made to FIG. 2 and FIG. 3 showing an example of a bond 20 pertaining to a measuring system 10 used in experiments. An adhesive 18 is applied to mating parts of a member 16 and a member 17 and the mating parts of the two members 16, 17 are brought together and bonded with the adhesive 18, and before or after the bonding the sensor part 14 of an optical fiber sensor 12 is embedded in the adhesive 18.

In the embedding of the sensor part 14, a thermosetting adhesive is used as the adhesive 18 for bonding the members 16 and 17 and is hardened at a temperature higher than room temperature and then returned to room temperature. At this time, due to a difference in the thermal expansivities of the adhesive 18 and the sensor part 14, a stress arises between the adhesive 18 and the sensor part 14. Because of this, a compressive or tensile strain arises in the sensor part 14. Whether the strain is a compressive strain or a tensile strain depends on the stress. The following description is based on the example of a compressive strain.

Next, the principle of measurement of the measuring system 10 according to the separation inspection method of the invention will be explained using FIG. 4.

Figure 4:
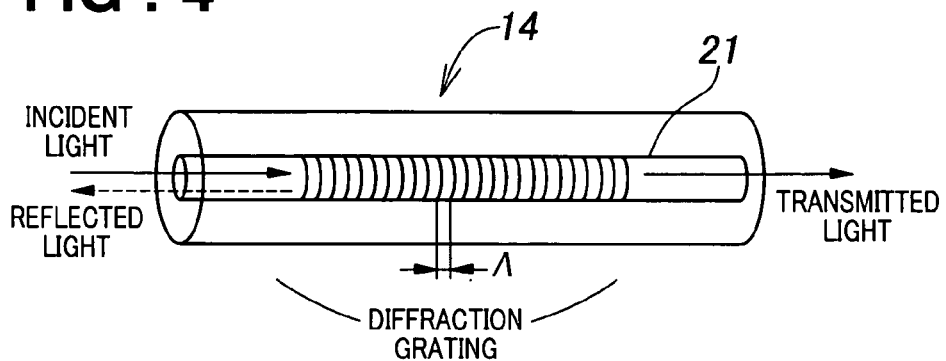
FIG. 4 is a schematic view of an optical fiber grating sensor.

FIG. 4 is a schematic view of a sensor part of an optical fiber grating sensor. The sensor part 14 of an optical fiber grating sensor used as an optical fiber sensor has cycles of light wavelength order written into the fiber core part 21 by the refractive index of the core part being made to change periodically, and has the function of reflecting light of a predetermined wavelength by using a coupling of forward and return modes propagating through the core part 21. The wavelength $\lambda_B$ that is coupled is shown by Exp. (1) using the effective refractive index of the propagating mode nEFF and the refractive index period $\Lambda$.

$$\lambda_B = 2n_{core}\Lambda \quad (1)$$

The reflectance R is obtained using the refractive index change $\Delta n$, the grating length L and the confinement rate $\eta c$ of propagating light to the core part, by Exp. (2).

$$R_B = \tan h^2(\pi L \cdot \Delta n \cdot \eta c / \lambda_B) \quad (2)$$

Figure 5:
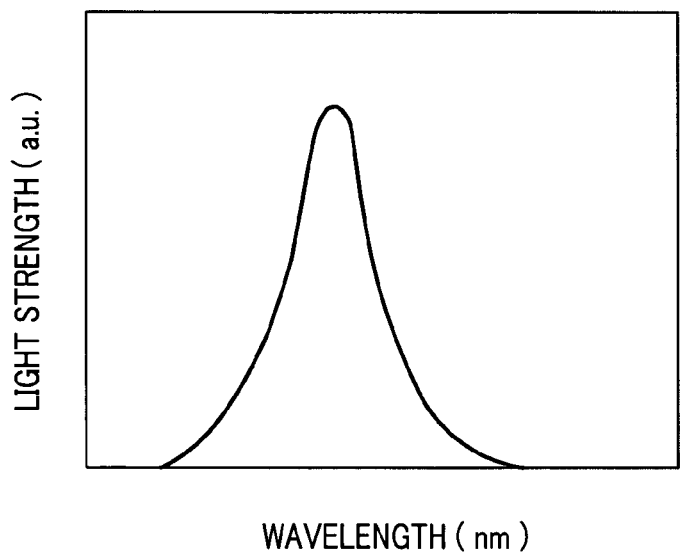
FIG. 5 is a graph showing a characteristic of light reflected from an optical fiber grating sensor.

For example, in the case of an optical fiber grating sensor used for wavelength separation in 1.55 µm band wavelength multiplex transmission, refractive index cycles of period $\Lambda$=approximately 0.5 µm are written over a length L of 10 mm, making 20,000 layers, and a very steep reflection characteristic is formed, as shown in FIG. 5.

Figure 6:
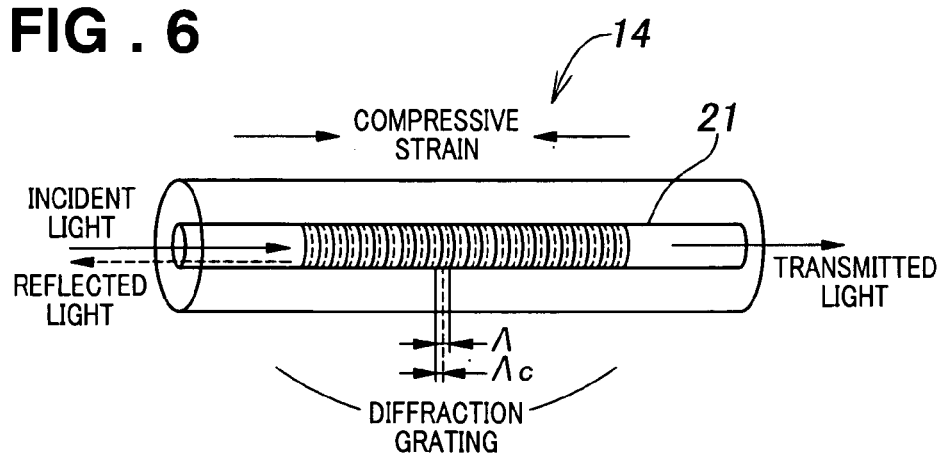
FIG. 6 is a schematic view of a sensor part under a compressive strain.
Figure 7:
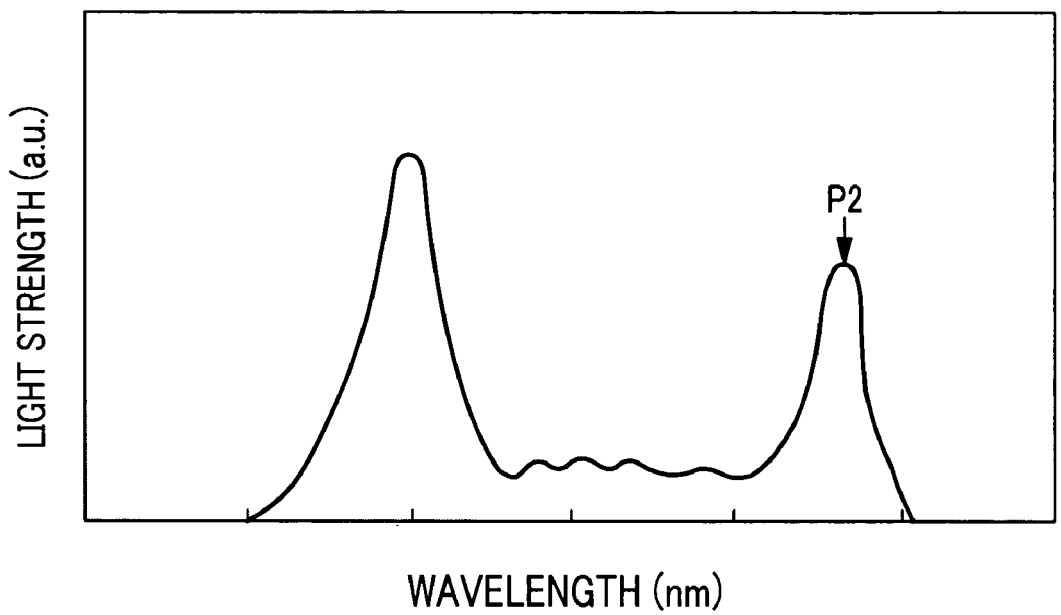
FIG. 7 is a graph showing a characteristic of light reflected from an optical fiber grating sensor when separation has occurred in a bond.

When this kind of sensor part 14 undergoes a compressive strain, the refractive index period $\Lambda$ shortens to $\Lambda c$ as shown in FIG. 6, and in accordance with Exp. (1) the $\lambda_B$ that is coupled shortens, that is, the wavelength of the reflected light shortens. When on the other hand the compressive strain decreases, parts where the refractive index period $\Lambda$ is close to the period of when there is no strain arise, the wavelength of reflected light from those parts becomes long, and, as shown in FIG. 7, a reflection peak P2 arises on the long-wavelength side also. When separation occurs, at the separated part, the compressive strain either decreases or ceases to exist, and a reflected light spectrum in which a there is reflection peak also on the long-wavelength side of the kind shown in FIG. 7 is obtained.

By observing the spectrum of reflected light with the measuring system 10 on the basis of the principle explained above, it is possible to detect separation of an inner or outer part of the adhesive or of its outside face.

Next, using FIG. 8 and FIG. 9, a first test example of a first embodiment using the measuring system 10 shown in FIG. 1 will be described.

Figure 8:
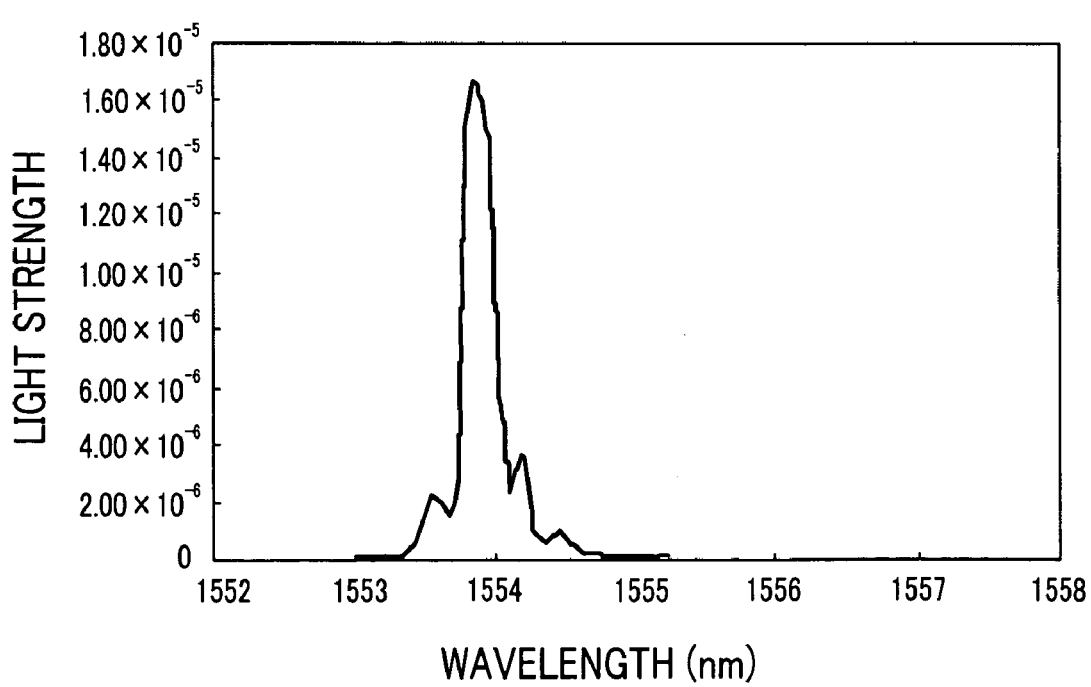
FIG. 8 is a spectrum of light reflected before separation when a sensor part was embedded in a 250° C. thermosetting adhesive.
Figure 9:
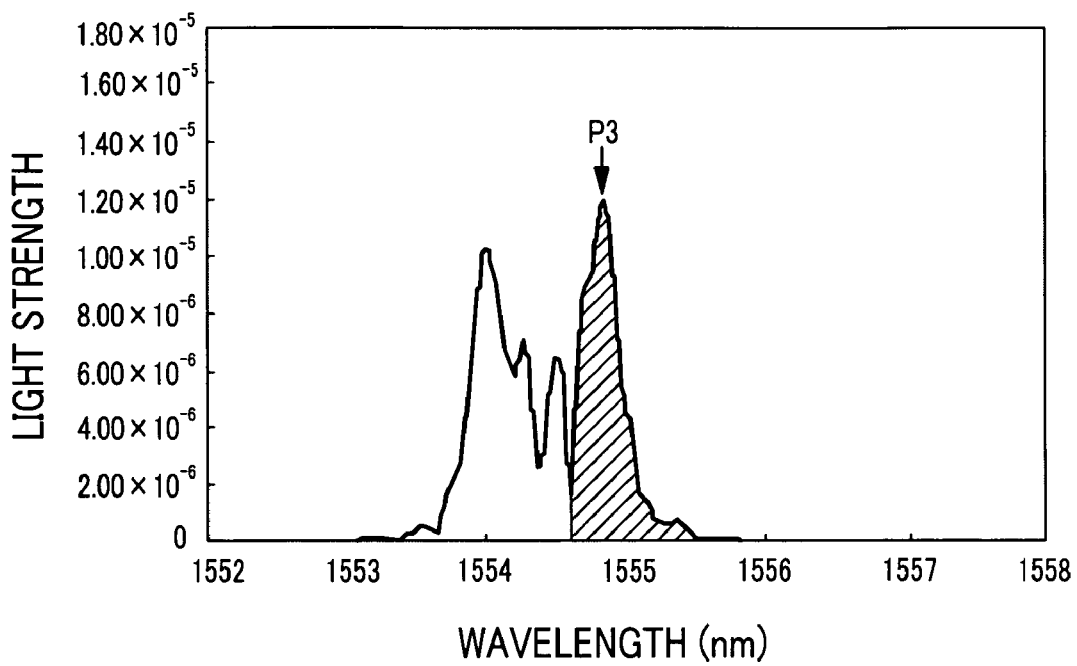
FIG. 9 is a spectrum of light reflected after separation when a sensor part was embedded in a 250° C. thermosetting adhesive.

FIG. 8 is a spectrum of reflected light of before separation when the sensor part 14 was embedded in a 250° C. thermosetting adhesive. The horizontal axis is wavelength and the vertical axis is light strength. At this time, a compressive strain has arisen in the sensor part as a result of thermal stress caused by differential thermal expansion between the adhesive and the optical fiber sensor, and a peak can be seen around 1554 nm.

Figure 10:
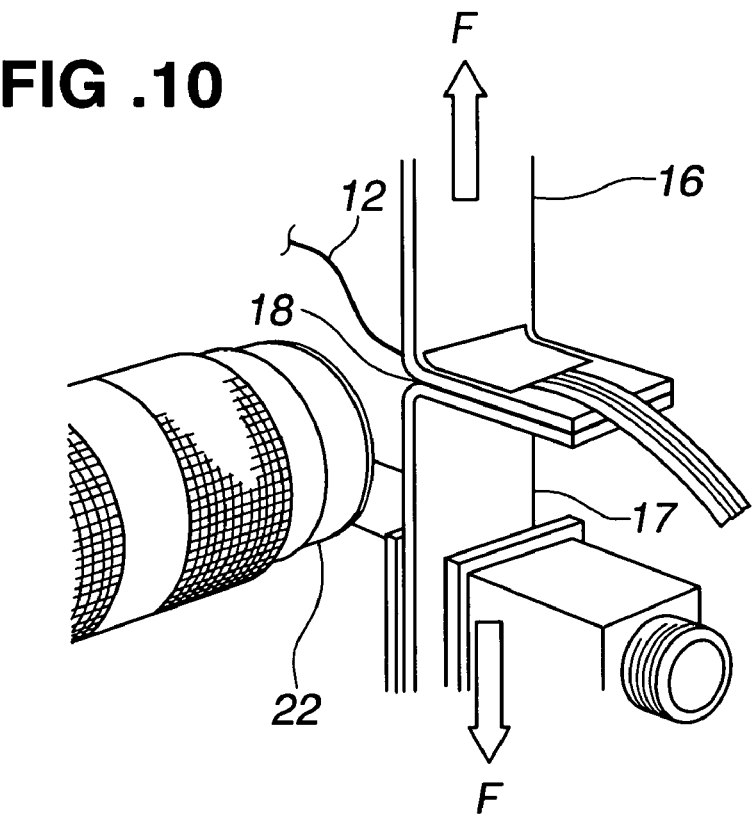
FIG. 10 is a view showing joined members being observed with a magnifying lens as a load is applied to them.

Next, as shown in FIG. 10, while the progress of separation is observed from the side of the bond 20 with a magnifying lens 22, a load (load F) is progressively applied to the members 16, 17 in a direction such that separation occurs in the adhesive 18. Until separation occurs, there is almost no change in the spectrum of reflected light obtained with the optical fiber sensor. When separation occurs and this separation can be confirmed with the magnifying lens 22, the load applied to the members 16, 17 is made zero. The reflected light spectrum obtained with the optical fiber sensor at that time is shown in FIG. 9. The spectrum changes greatly when separation occurs, and at 1555 nm also a peak P3 arises. This is presumably because when separation occurs there ceases to be stress between the adhesive and the sensor part where the separation has occurred, and as a result an unstrained part arises in the sensor part 14.

By this measurement, when separation has occurred in the adhesive 18, because a peak arises also on the long-wavelength side, it is possible to detect separation surely by observing this peak.

If the measuring system 10 described above is used to monitor the state of a bond of an aircraft fuselage and the reflected light spectrum obtained with the optical fiber sensor 12 is measured, because when separation has not occurred in the bond 20 there is one peak in the reflected light spectrum on the short-wavelength side and when separation has occurred in the bond 20 another peak in the reflected light spectrum appears on the long-wavelength side in addition to the one on the short-wavelength side, it is possible to determine accurately whether or not the adhesive has separated on the basis of whether this peak has appeared.

Although in the measuring system 10 described above the reflected light spectrum was measured using an optical spectrum analyzer as the light-detecting part 13, alternatively a photodiode having sensitivity to a certain specified wavelength may be used to detect the strength of the light at that wavelength, and for example by using a photodiode having sensitivity to the wavelength 1555 nm arising when separation occurs and monitoring its detection value, separation may be detected on the basis of an increase in that strength.

Figure 11:
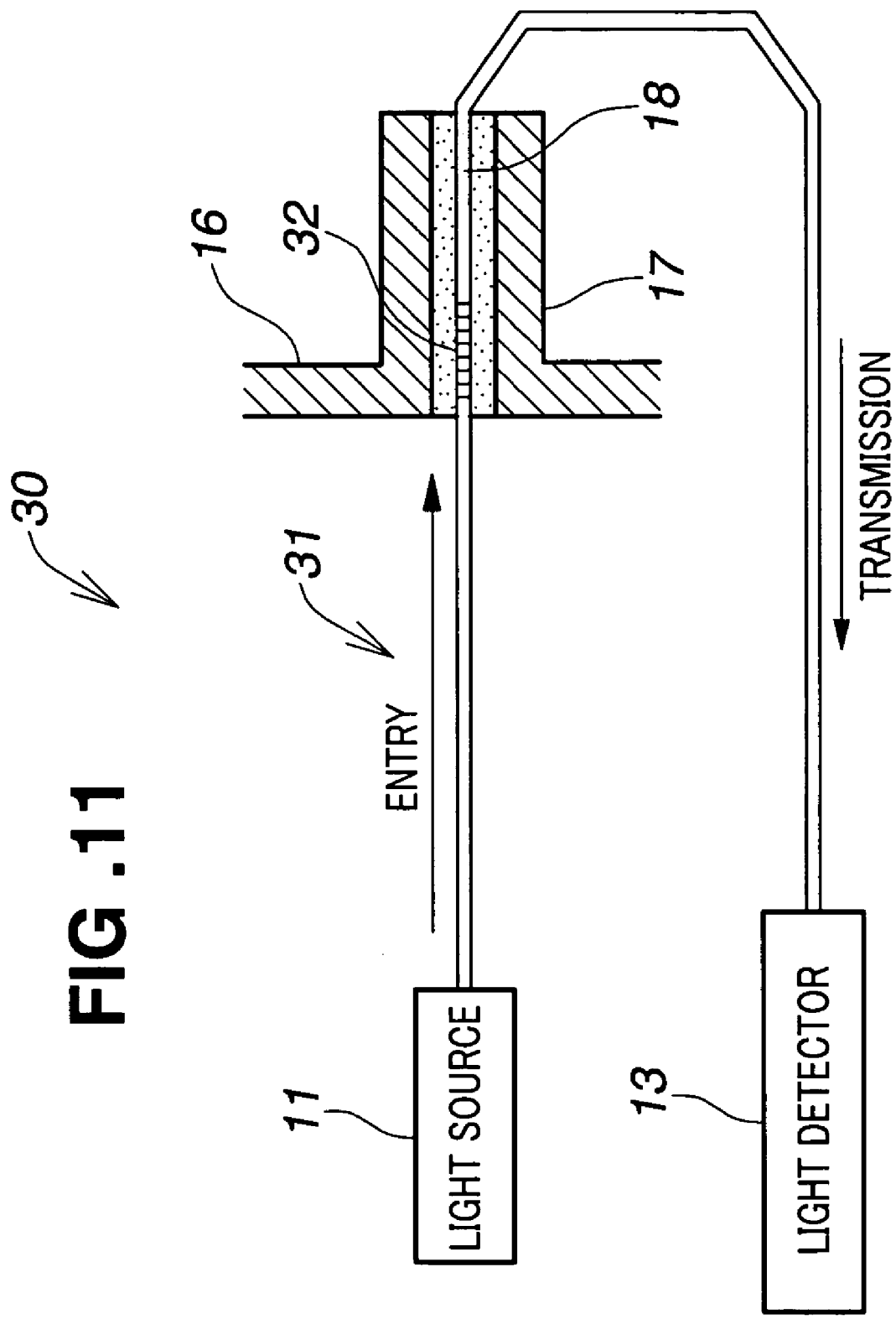
FIG. 11 is a basic construction view of a measuring system used in a bond separation inspection method according to a second preferred embodiment of the invention.

FIG. 11 is a basic construction view of a measuring system for carrying out a bond separation inspection method according to a second preferred embodiment of the invention. This measuring system 30 is made up of a light source 11, an optical fiber sensor 31 and a light-detecting part 13.

The light source 11 and the light-detecting part 13 are the same as in the first preferred embodiment shown in FIG. 1, and accordingly the same reference numerals have been assigned to them and they will not be described again here.

The optical fiber sensor 31 has a sensor part 32; light from the light source 11 is guided into the sensor part 32, and light transmitted through the sensor part is detected. One end of the optical fiber is connected to the light source 11, and the sensor part 32 is embedded in an adhesive 18 when members 16, 17 are joined together.

In the same way as in the first preferred embodiment, a measuring system 30 is formed using an optical fiber grating sensor and using a thermosetting adhesive as the adhesive for joining the members 16, 17 under the same conditions as those described above. At this time, differential thermal expansion between the adhesive and the optical fiber sensor is made to cause a compressive strain in the sensor part.

As the light-detecting part 13 shown in FIG. 11, an optical spectrum analyzer for obtaining a transmission spectrum of transmitted light from the sensor part 32 is used.

Next, the principle of measurement by the measuring system 30 of the separation inspection method of this invention will be explained.

The sensor part 32 is the same as in the first preferred embodiment except that it is formed part-way along the optical fiber sensor 31: it has cycles of light wavelength order written into the fiber core part, and has the function of reflecting light of a predetermined wavelength by using a coupling of forward and return modes propagating through the core part. The wavelength $\lambda_B$ that is coupled is shown by Exp. (1) using the effective refractive index of the propagating mode $N_{EFF}$ and the refractive index period $\Lambda$.

The reflectance R is obtained using the refractive index change $\Delta n$, the grating length L and the confinement rate $1c$ of propagating light to the core part, by Exp. (2).

Figure 12:
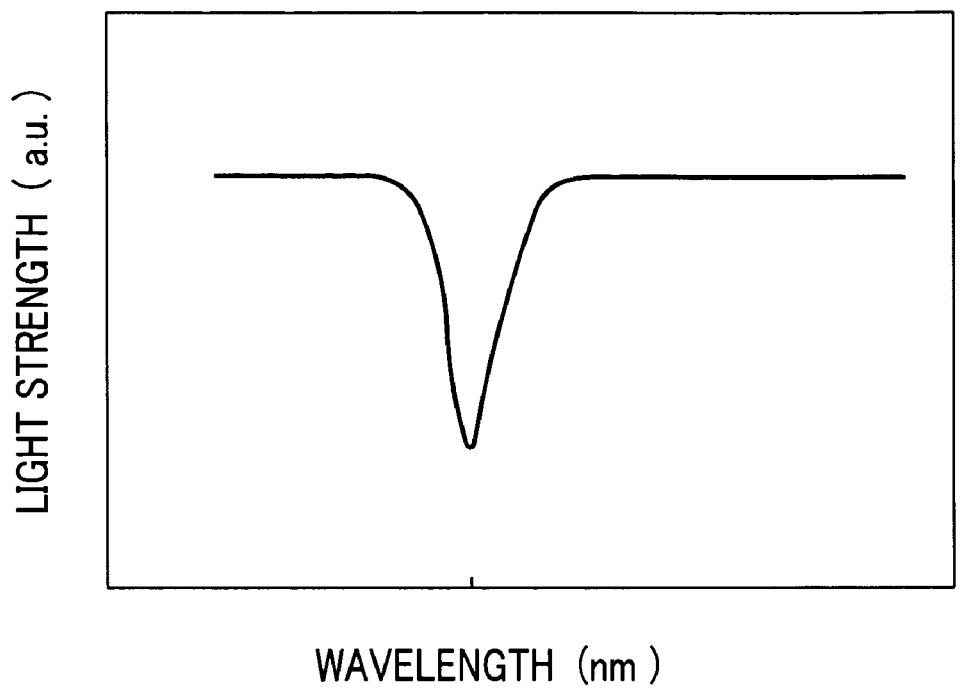
FIG. 12 is a graph showing a characteristic of transmission through an optical fiber grating sensor.

For example, in the case of an optical fiber grating sensor used for wavelength separation in 1.55 μm band wavelength multiplex transmission, refractive index cycles of period $\Lambda$=approximately 0.5 μm are written over a length L of 10 mm, making 20,000 layers, and a very steep transmission characteristic is formed, as shown in FIG. 12.

Figure 13:
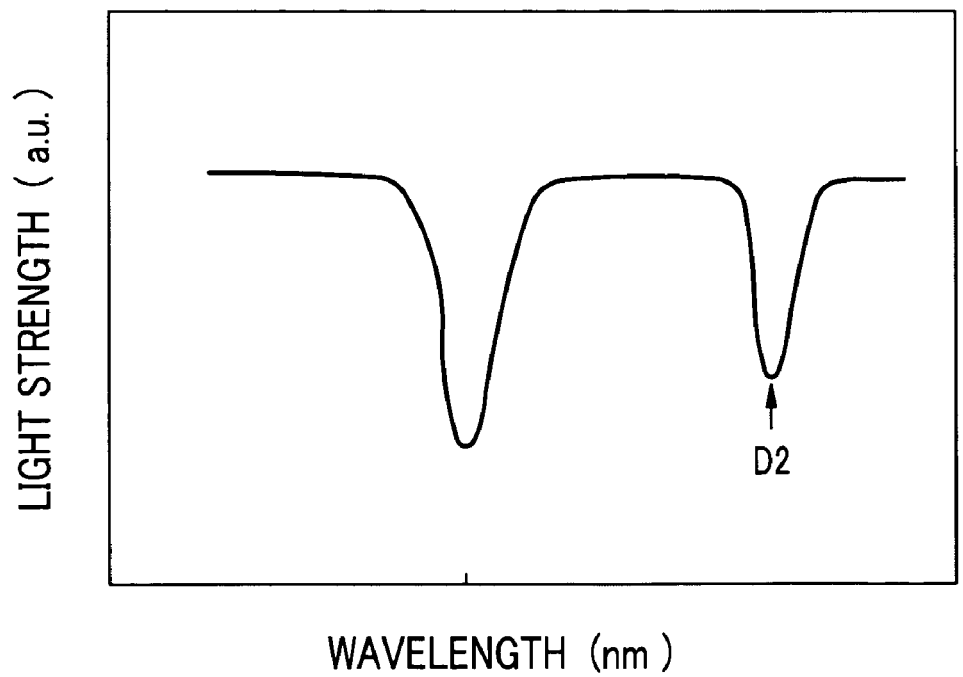
FIG. 13 is a graph showing a characteristic of light transmitted through an optical fiber grating sensor when separation has occurred in a bond.

When this kind of sensor part 32 undergoes a compressive strain, the refractive index period $\Lambda$ shortens to $\Lambda c$ as shown in FIG. 6, and in accordance with Exp. (1) the wavelength of the reflected light shortens. When on the other hand the compressive strain decreases, parts where the refractive index period $\Lambda$ is close to the period of when there is no strain arise, the wavelength of reflected light from those parts becomes long, and, as shown in FIG. 13, a transmission dip D2 arises on the long-wavelength side also. When separation occurs, at the separated part, the compressive strain either decreases or ceases to exist, and a transmission dip appears on the long-wavelength side also.

By observing the spectrum of transmitted light with the measuring system 30 on the basis of the principle explained above, it is possible to detect separation of the bond.

If the measuring system 30 described above is used for example to monitor the state of a bond of an aircraft fuselage and the transmitted light spectrum is measured, because when the bond has not separated there is one dip in the transmitted light spectrum on the short-wavelength side and when the bond has separated another dip in the transmitted light spectrum appears on the long-wavelength side in addition to the one on the short-wavelength side, it is possible to determine accurately whether or not the adhesive has separated on the basis of whether this dip has appeared.

In the measuring system 30 described above the transmitted light spectrum was measured using an optical spectrum analyzer as the light-detecting part 13. However, alternatively a photodiode or the like having sensitivity to a certain specified wavelength may be used to detect the strength of the light at that wavelength. For example, by using a photodiode having sensitivity to the wavelength 1555 nm arising when separation occurs and monitoring its detection value, separation may be detected on the basis of a decrease in that strength.

Next, a third preferred embodiment of the invention will be described. The measuring system of this third preferred embodiment is the same as the measuring system 10 described in the first preferred embodiment. In the measuring system of this third preferred embodiment, also, the following predetermined loads are applied to the members 16, 17, and the occurrence or otherwise of separation of the bond is detected from a change in the optical characteristics of light obtained with an optical fiber sensor under these conditions.

In this third preferred embodiment, instead of the thermosetting adhesive mentioned in the first preferred embodiment, alternatively the two members 16, 17 can be joined using an adhesive that hardens at room temperature as the adhesive 18.

As the predetermined load, an external force such as will elastically deform the structure constituted by the two members 16, 17 joined by means of the adhesive 18 is applied. When there is a possibility of causing separation in the adhesive 18, the external force is preferably applied in a direction such that the separation will increase.

Figure 14:
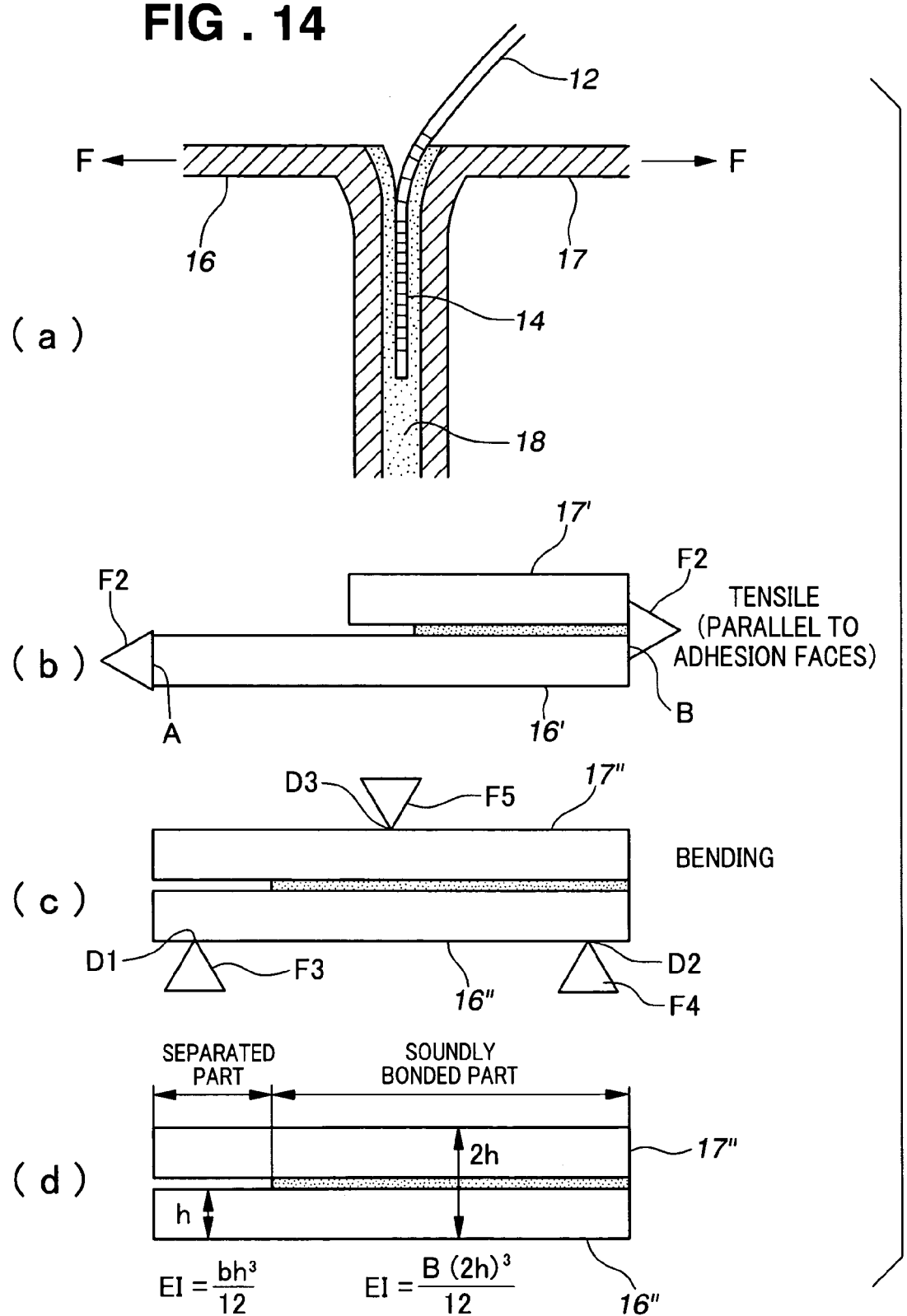
FIG. 14(a) to (d) are schematic views illustrating loads applied to members, FIG. 14A illustrating the application of a tensile load of a direction approximately perpendicular to adhesion faces and tending to increase separation, FIG. 14(b) of a parallel tensile load and FIG. 14(c) of a bending load, and FIG. 14(d) being a view illustrating the respective flexural rigidities (EI) of joined members where an adhesive has separated (separated part) and where the adhesive has not separated (soundly bonded part)

As shown in FIG. 14(a), an external force F is applied as a tensile load in a direction substantially perpendicular to the faces of the adhesive 18 adhered to the members 16, 17 so that the separation increases, or, with a joined member made by joining together members 16', 17' of the kind shown in FIG. 14(b), an external force F2 is applied as a tensile force parallel with the end faces A, B of the joined member. In a joined member made by joining together members 16", 17" of the kind shown in FIG. 14(c), external forces F3, F4 and F5 are applied as a bending load to three points D1, D2 and D3 on the joined member. The measuring system is the same as the measuring system 10 described with reference to FIG. 1, and accordingly its construction will not be described again here.

Next, the principle of measurement of the separation inspection method of the third preferred embodiment of the invention will be explained.

An optical fiber grating sensor has cycles of light wavelength order written into the fiber core part and has the function of reflecting light of a predetermined wavelength by using a coupling of forward and return modes propagating through the core part. The wavelength $\lambda_B$ that is coupled is shown by Exp. (1) using the effective refractive index of the propagating mode $n_{EFF}$ and the refractive index period $\Lambda$.

The reflectance R is obtained using the refractive index change $\Delta n$, the grating length L and the confinement rate $1c$ of propagating light to the core part, by Exp. (2).

When this sensor part undergoes a compressive strain, its refractive index period $\Lambda$ shortens to $\Lambda c$, as shown in FIG. 6, and the reflected wavelength shortens. When on the other hand the compressive strain decreases, parts where the refractive index period $\Lambda$ is close to the period of when there is no strain arise, the wavelength of reflected light from those parts becomes long, and, as shown in FIG. 7, a reflection peak P2 arises on the long-wavelength side also. When separation occurs, at the separated part, the compressive strain either decreases or ceases to exist. Because as a result of the load being applied to the members 16, 17, as shown in FIG. 14(a), a tensile strain arises in the sensor part of the optical fiber sensor, the grating period $\lambda$ shown in FIG. 6 becomes still longer. At this time, the rigidity of the bond falls greatly as a result of the adhesive separating and its plate thickness changing.

FIG. 14(d) shows the flexural rigidity of a part where the adhesive of the bond has separated and of a part where the adhesive has not separated. If the thickness of the members 16" and 17" is written h and their width b, the flexural rigidity at the part where the adhesive has not separated (a value expressing the reluctance of a member to bend) EI is given by $EI=Eb(2h)^3/12$ (here, E is the Young's modulus of the member and I is the geometrical moment of inertia) and the flexural rigidity EI of the part where the adhesive has separated is given by $EI=Ebh^3/12$. At this time, the flexural rigidity EI of the part where the adhesive has separated is ⅛ of the flexural rigidity EI of the part where the adhesive has not separated. Here the rigidity C is also smaller at the separated part than at the non-separated part. The rigidity C is expressed as C=P/U. Here, P is the load and U the strain. Therefore, when the rigidity C becomes small, even if the same load P is applied to the part where separation has occurred and the part where separation has not occurred, the strain U is greater in the part where separation has occurred than in the part where separation has not occurred.

Consequently, when separation has occurred the sensor part of the optical fiber sensor undergoes a larger strain than when separation has not occurred, and a peak arises in the reflected light spectrum further to the long-wavelength side than shown in FIG. 7.

On the basis of this principle, in the measuring system described above it is possible to detect separation of a bond surely by observing the peaks in the reflected light spectrum when a load is applied to the member.

Next, a test example of the third preferred embodiment will be described.

SECOND TEST EXAMPLE

In this embodiment, the reflected light spectrum of before separation when a sensor part was embedded in a 250° C. thermosetting adhesive is as shown in FIG. 8, discussed with reference to the first preferred embodiment, in which the horizontal axis is wavelength and the vertical axis is light strength. At this time, a peak appears in the vicinity of 1554 nm. As shown in FIG. 10, the load is progressively increased as the joined member is observed with a magnifying lens. Until separation occurs, there is almost no change in the spectrum, and when separation occurs the load is brought to zero. The spectrum in this case is as shown in FIG. 9. When separation occurs the spectrum changes greatly, and another peak arises at 1555 nm. This is presumably the result of a part which has ceased to be under compressive strain arising in the sensor part.

Figure 15:
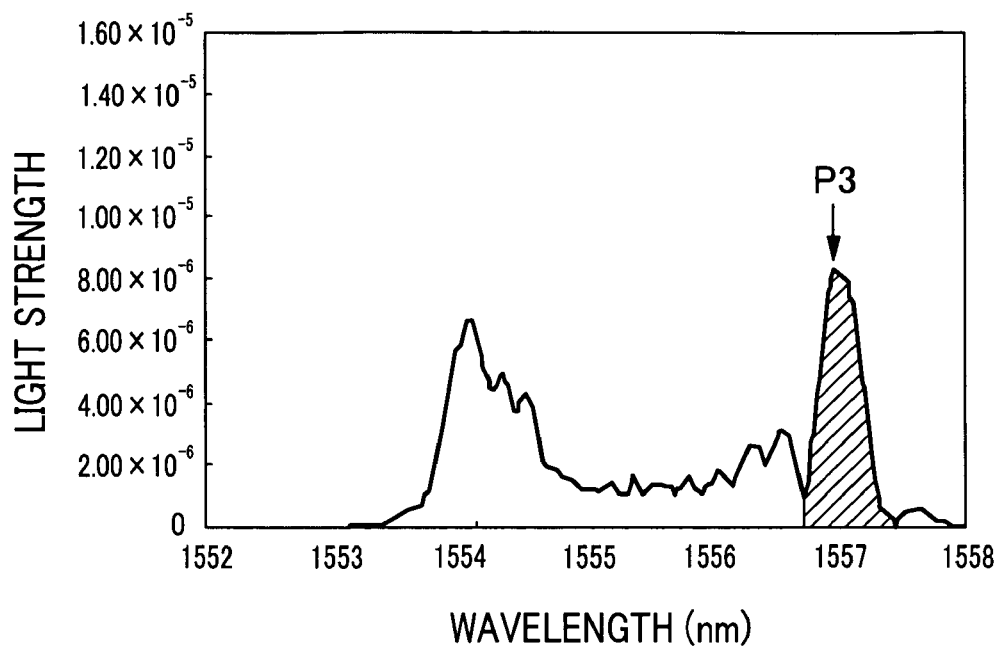
FIG. 15 is a spectrum of light reflected when separation has occurred and a load has been applied.

Also, when a load of about 10 kg is applied, the kind of reflected light spectrum shown in FIG. 15 is obtained, and the peak appears as a peak P3 shifted to the long-wavelength side compared to the first preferred embodiment.

From the above measurement, because a peak arises further to the long-wavelength side, it is possible to detect separation by measuring this peak.

THIRD TEST EXAMPLE

Figure 16:
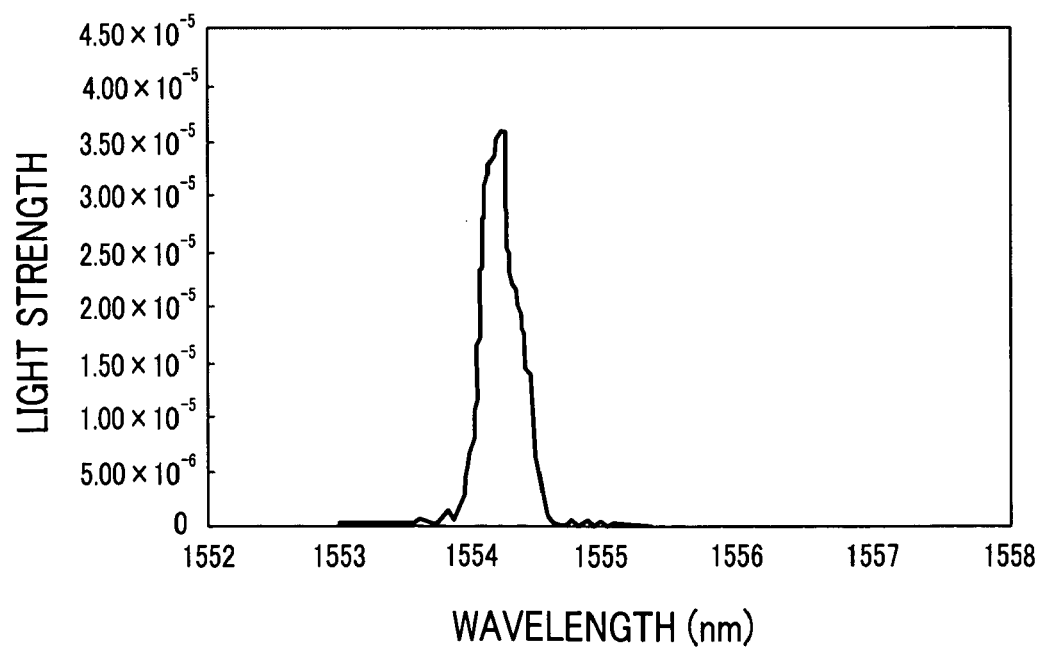
FIG. 16 is a spectrum of light reflected before separation when a sensor part was embedded in an adhesive which hardens at room temperature.
Figure 17:
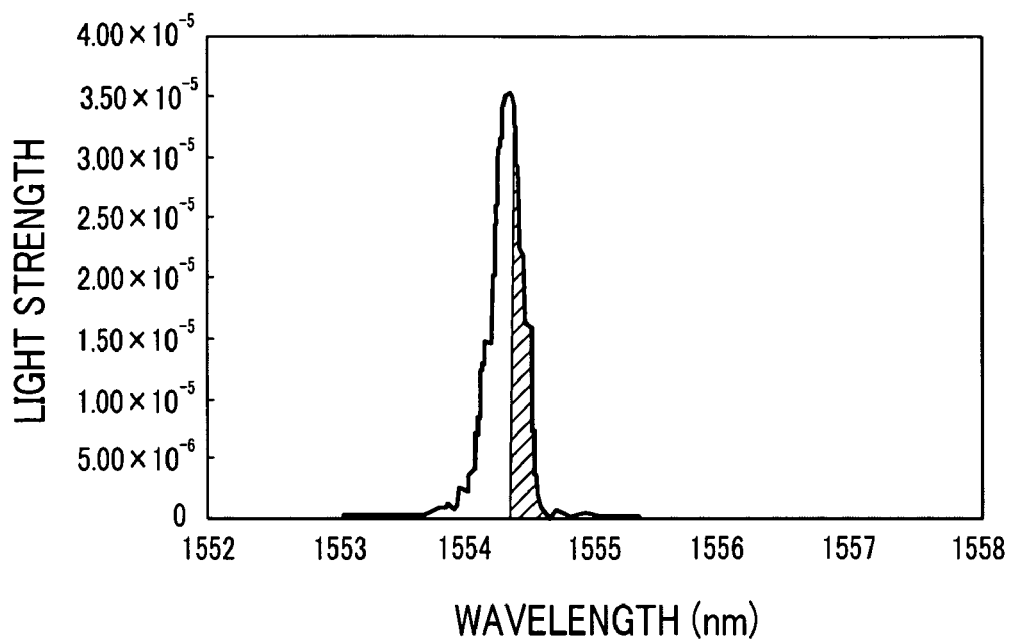
FIG. 17 is a spectrum of light reflected when a sensor part was embedded in an adhesive which hardens at room temperature and separation has occurred but no load is being applied.
Figure 18:
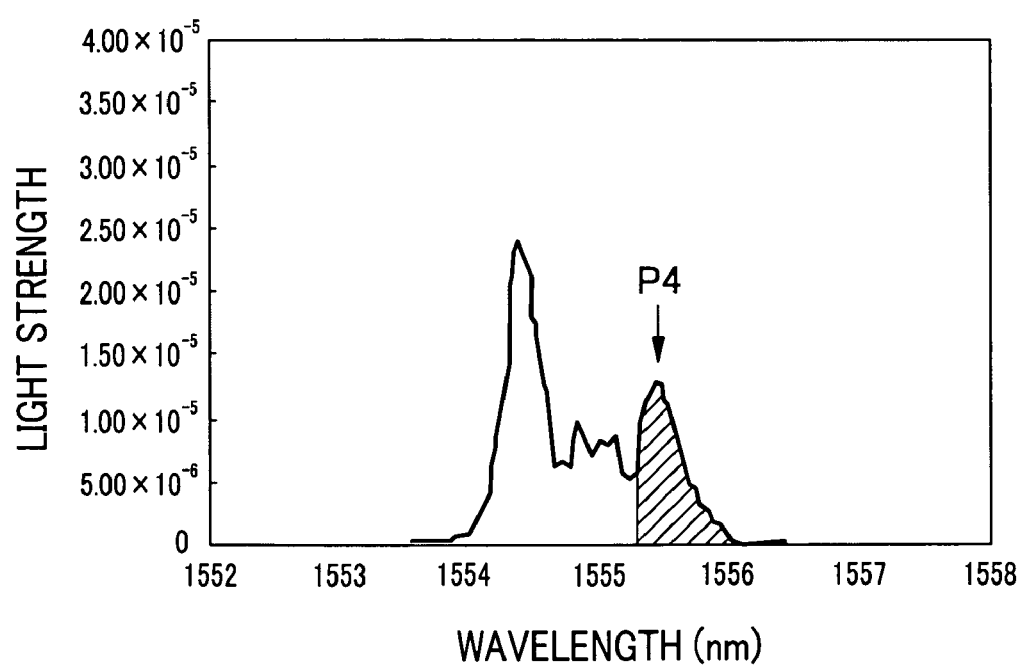
FIG. 18 is a spectrum of light reflected when a sensor part was embedded in an adhesive which hardens at room temperature and separation has occurred and a load is being applied.

In this test example, the members 16, 17 are bonded with an adhesive that hardens at room temperature. FIG. 16 is the reflected light spectrum of before separation when the sensor part was embedded in a room temperature setting adhesive. In FIG. 16, the horizontal axis is wavelength and the vertical axis is light strength. At this time, a peak appears in the vicinity of 1554 nm. As shown in FIG. 10, a load is progressively increased as the joined member is observed with a magnifying lens. Until separation occurs, there is almost no change in the spectrum, and when separation occurs the load is brought to zero. The spectrum at this time is shown in FIG. 17. The spectrum does not change much even when separation occurs. This is presumably because since the adhesive hardens at room temperature the compressive strain is small compared to an adhesive which hardens at a high temperature. FIG. 18 shows the reflected light spectrum of when the load was further increased. At this time, a peak P4 arises on the long-wavelength side.

From the above measurement, because when separation occurs and a load is applied a peak arises also on the long-wavelength side, by observing this peak it is possible to detect separation. As an application of this, when monitoring the state of a bond of an aircraft fuselage, if the reflection characteristic of at the time of manufacture of the fuselage and the reflection characteristic of when the fuselage is pressurized on the ground after an actual flight are measured and compared, it is possible to determine accurately whether or not separation has occurred.

A fourth preferred embodiment of the invention will now be described. This fourth preferred embodiment is a construction wherein a predetermined load of the kind discussed in the third preferred embodiment is applied to the members 16, 17 in a construction using the measuring system 30 discussed in the second preferred embodiment. The predetermined load is as discussed with reference to FIGS. 14(*a*) through (*d*), and the principle of measurement is the same as the principle explained in the third preferred embodiment except that the system is of the transmission type.

Obviously, various minor changes and modifications of the present invention are possible in the light of the above teaching. It is therefore to be understood that within the scope of the appended claims the invention may be practiced otherwise than as specifically described.

What is claimed is:

1. A bond separation inspection method comprising:
   joining together two members with an adhesive;
   embedding a sensor part of an optical fiber sensor in the adhesive;
   introducing light from a light source into one end of the optical fiber sensor and causing light from the sensor part to emerge from another end of the optical fiber sensor; and
   detecting separation of the bond of the two members on the basis of an optical characteristic of the light from the sensor part,
   wherein embedding the sensor part in the adhesive includes causing a compressive thermal strain to arise in the sensor part due to different thermal expansivities of the adhesive and the sensor part so a refractive index period of the sensor part is sufficiently reduced such that a wavelength of reflected light emerging from the another end of the optical fiber caused by a bond separation is separated from a wavelength of reflected light caused inherently by the sensor part.

2. The bond separation inspection method according to claim 1, wherein causing the compressive strain in the sensor part comprises using a thermo-setting adhesive as the adhesive and hardening the adhesive at a temperature higher than room temperature and then returning it to room temperature.

3. The bond separation inspection method according to claim 1, wherein the optical fiber sensor is an optical fiber grating sensor.

4. The bond separation inspection method according to claim 1, wherein the light source is a broadband light source.

5. The bond separation inspection method according to claim 1, wherein the optical characteristic is an optical characteristic of reflected light reflected in the sensor part.

6. The bond separation inspection method according to claim 1, wherein the optical characteristic is an optical characteristic of transmitted light passing through the sensor part.

7. The bond separation inspection method according to claim 5, wherein the optical characteristic of the reflected light is a spectrum characteristic of the reflected light.

8. The bond separation inspection method according to claim 5, wherein the optical characteristic of the reflected light is a strength characteristic of the reflected light at a predetermined wavelength.

9. The bond separation inspection method according to claim 6, wherein the optical characteristic of the transmitted light is a spectrum characteristic of the transmitted light.

10. The bond separation inspection method according to claim 6, wherein the optical characteristic of transmitted light is a strength characteristic of the transmitted light at a predetermined wavelength.

11. The bond separation inspection method according to claim 1, further comprising:

applying a predetermined load to the two members.

12. The bond separation inspection method according to claim 11, wherein the predetermined load is a load applied to the two members in a direction such that it tends to increase any separation of the bond.

13. The bond separation inspection method according to claim 11, wherein applying the load comprises applying external forces which deform the two members elastically.

14. The bond separation inspection method according to claim 1, wherein the refractive index period is reduced by at least 50% caused by the thermal compressive strain.

* * * * *

UNITED STATES PATENT AND TRADEMARK OFFICE
CERTIFICATE OF CORRECTION

PATENT NO. : 7,041,960 B2 Page 1 of 1
APPLICATION NO. : 10/824353
DATED : May 9, 2006
INVENTOR(S) : Keiichi Sato et al.

It is certified that error appears in the above-identified patent and that said Letters Patent is hereby corrected as shown below:

Title page, item (75), please added the following named inventor:

Kazuro KAGEYAMA

Signed and Sealed this

Fourteenth Day of November, 2006

JON W. DUDAS
*Director of the United States Patent and Trademark Office*